United States Patent [19]

Ni et al.

[11] Patent Number: 5,061,494
[45] Date of Patent: Oct. 29, 1991

[54] TRI-SCORED DRUG TABLET

[75] Inventors: Phillip F. Ni, Mattawan; Larry F. Odar, Galesburg, both of Mich.

[73] Assignee: The Upjohn Comany, Kalamazoo, Mich.

[21] Appl. No.: 655,266

[22] Filed: Feb. 13, 1991

Related U.S. Application Data

[63] Continuation of Ser. No. 499,475, Jun. 14, 1990, abandoned.

[51] Int. Cl.$^5$ ............................................... A61K 9/44
[52] U.S. Cl. ..................................... 424/467; 424/400
[58] Field of Search ......................................... 424/467

[56] References Cited

U.S. PATENT DOCUMENTS

| D. 202,467 | 10/1965 | Gullmot | D16/3 |
|---|---|---|---|
| D. 216,307 | 12/1969 | Ninger | D16/3 |
| D. 220,956 | 6/1971 | Roberts | D16/3 |
| D. 224,591 | 8/1972 | Roberts | D16/1 |
| D. 228,456 | 9/1973 | Ninger | D16/1 |
| D. 310,579 | 9/1990 | Ni et al. | D28/2 |
| 2,052,376 | 8/1936 | Zellers | 167/53 |
| 3,336,200 | 8/1967 | Krause et al. | 424/463 |
| 4,215,104 | 7/1980 | Ullman et al. | 424/467 |
| 4,258,027 | 3/1981 | Ullman et al. | 424/15 |
| 4,735,805 | 4/1988 | Ni et al. | 424/464 |

FOREIGN PATENT DOCUMENTS

| 8632046 | 3/1987 | Fed. Rep. of Germany . |
| 993291 | 5/1965 | United Kingdom . |
| 2057878 | 4/1981 | United Kingdom . |

Primary Examiner—Thurman K. Page
Assistant Examiner—Leon R. Horne
Attorney, Agent, or Firm—Flynn, Thiel, Boutell & Tanis

[57] ABSTRACT

A tri-scored drug tablet having an elongated tablet body with a length greater than its width. The body has a bottom facing surface with a pair of concavities therein. Each concavity is equal in size and has parallel major and minor axes, each concavity further having a smooth and uninterrupted arcuate surface extending between the opposite longitudinal ends of said body and a longitudinally central part of said tablet. The opposite longitudinal ends of the body and the longitudinally central part are of a thicker dimension than the thickness of the body measured at an apex of each of the concavities. Aligned breaking grooves are formed in the top and bottom surfaces at both of the concavities and between the concavities at said longitudinally central part, each of breaking groove extending laterally across the width of said tablet at said apex of each of said concavities and at said longitudinally central part to divide the tablet into four quarter sections of equal size.

4 Claims, 2 Drawing Sheets

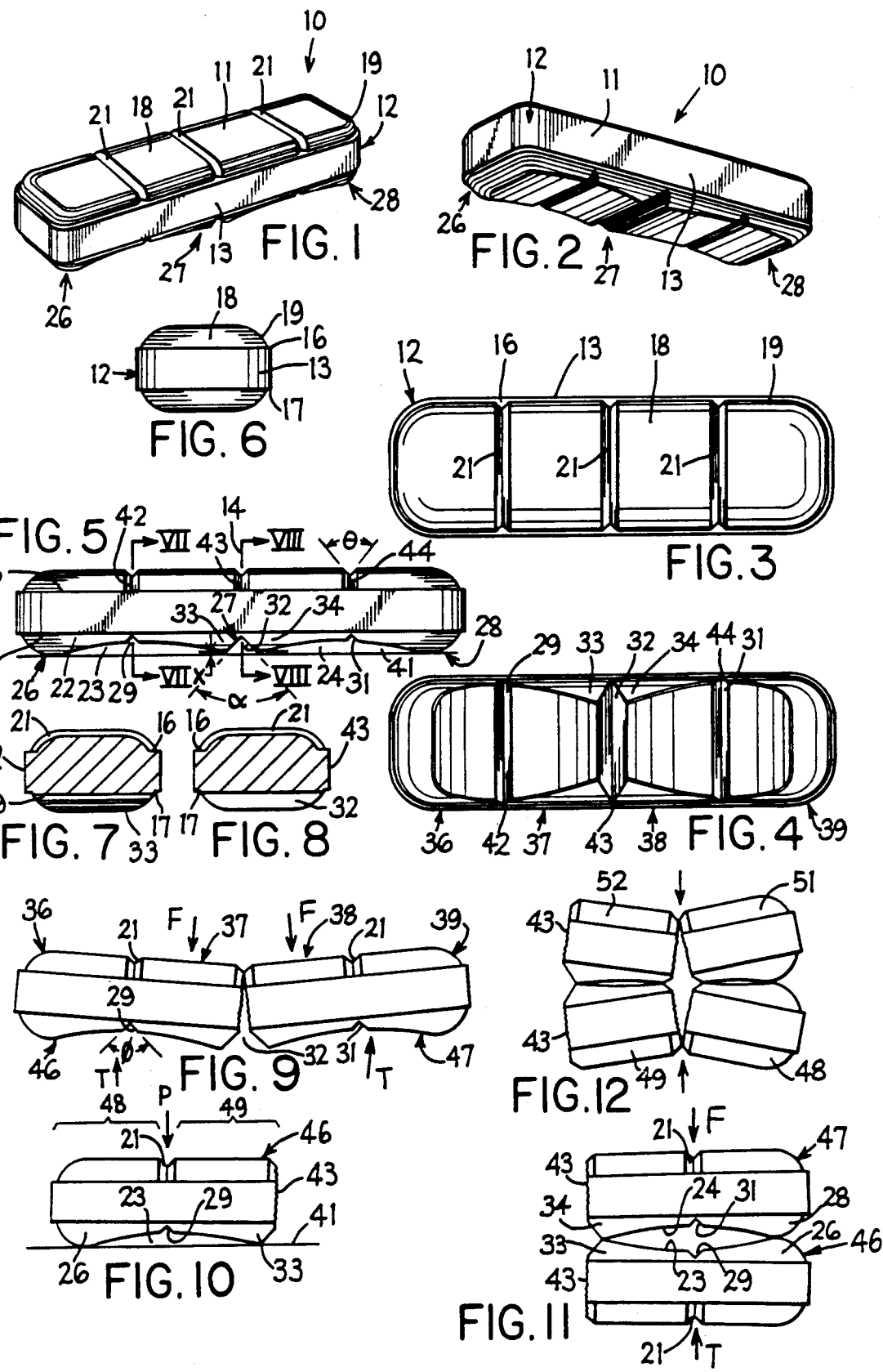

TRI-SCORED DRUG TABLET

This application is a continuation of U.S. Ser. No. 07/499 475, filed June 14, 1990 now abandoned.

FIELD OF THE INVENTION

This invention relates to a tri-scored drug tablet and, more particularly, to a tri-scored drug tablet having a length greater than its width and structure for facilitating a breaking of the tablet into four equal parts.

BACKGROUND OF THE INVENTION

Scored drug tablets have been known for many years and are provided to patients to enable them to break the tablet into two or more parts to enable fractional dosages of the medicine to be taken by the patient (see British Patent No. 993 291). Heretofore, problems have been encountered by the patient in facilitating a proper breakage of the tablet into its component parts due to the strength of the binder agents utilized to bind the active pharmacological agents contained within the tablet. Arthritic patients may be unable to break the tablet into its component parts due to the aforesaid strength characteristic. In some instances, a sharp edged tool, such as a knife, is needed in order to effect an even breakage of the tablet into its component parts. Further, and more important, is the requirement that the fractured tablet components contain the corresponding fraction, within the required ±15% limits, of active pharmacological agents in each of the divided sections.

It is an object of the present invention to provide a tri-scored drug tablet capable of being easily broken into four parts.

It is a further object of this invention to provide a tri-scored drug tablet, as aforesaid, capable of being broken into its component parts by simply holding the tablet between the thumb and forefinger and applying the requisite compressive breaking force.

It is a further object of this invention to provide a tri-scored drug tablet, as aforesaid, which has a length greater than its width and appropriate structure at its opposite longitudinal ends and longitudinally central part as well as structure defining a zone of weakness at the longitudinally central part and in the central region of each half section to facilitate a breakage of the tablet into separate but equal components.

It is a further object of this invention to provide a tri-scored drug tablet, as aforesaid, having the requisite strength characteristics to prevent premature breakage of the tablet either during manufacture, insertion into a container or during transit of the container to the end user.

It is a further object of this invention to provide a tri-scored drug tablet, as aforesaid, which is easy to manufacture and is of sufficient but yet minimum size to facilitate easy swallowing of the tablet by the end user patient.

SUMMARY OF THE INVENTION

The objects and purposes of the broadest aspect of the invention, including those set forth above, are met by providing a tri-scored drug tablet having an elongated tablet body with a length greater than its width. The tablet body also has a bottom surface with a pair of concavities being provided therein. Aligned breaking grooves are formed in the top and bottom surfaces. The breaking grooves in the bottom surface are provided in both of the concavities as well as at a longitudinally central part and extend laterally across the width of the tablet at an apex of each cavity and at the longitudinally central part. Thus, upon a user grasping both ends of the tablet between a forefinger and a thumb on each hand, a force is applied to effect a fracture of the tablet along the breaking groove at the longitudinally central part to divide the tablet into two half sections, the user thereafter placing the two half sections in a stacked arrangement so that the two concavities face one another and the thickest dimensioned portions at the longitudinal ends of the half sections are in engagement, the user thereafter applying a compressive force to the midpoint of the stacked half sections to effect a fracture of each of the halves along the breaking grooves at the apexes of the concavities to divide each of the half sections into two quarter sections.

BRIEF DESCRIPTION OF THE DRAWING

The subject matter of the invention will be described in more detail hereinafter in connection with the exemplary embodiments illustrated in the drawing, in which:

FIG. 1 is a left top perspective view of a tri-scored tablet embodying the invention;

FIG. 2 is a left bottom perspective view of the tablet;

FIG. 3 is a top view thereof;

FIG. 4 is a bottom view thereof;

FIG. 5 is a side view thereof;

FIG. 6 is an end view thereof;

FIG. 7 is a sectional view taken along the line VII—VII of FIG. 3;

FIG. 8 is a sectional view taken along the line VIII—VIII of FIG. 3;

FIG. 9 is a side view similar to FIG. 5 but with the tablet separated into two half sections;

FIG. 10 is a side view of a half section resting on a support surface;

FIG. 11 is a side view of two half sections, one stacked on the other;

FIG. 12 is a side view of the stacked half sections following the application of force causing a simultaneous breakage of each half section into two quarter sections;

DETAILED DESCRIPTION

Figure 13:
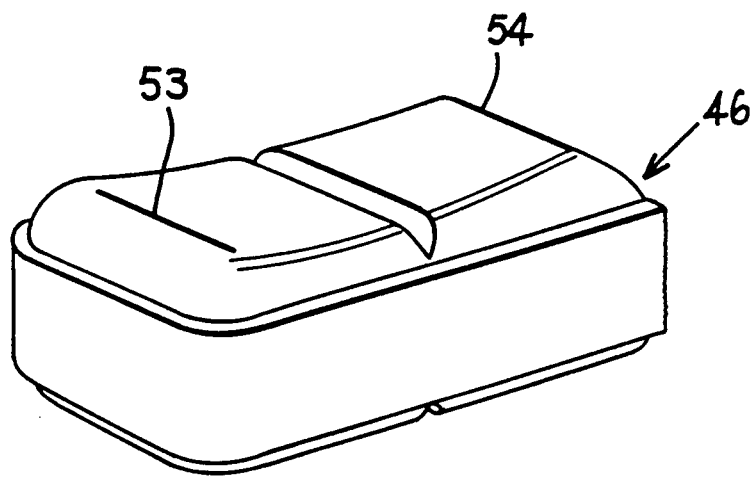
FIG. 13 illustrates a half section having an arcuate end, so that the opposing ends of the half sections will engage along a line.

A tri-scored drug tablet 10 is illustrated in a perspective view in FIGS. 1 and 2. FIG. 1 illustrates the drug tablet from the top and left end thereof. FIG. 2 illustrates the drug tablet from the bottom and left end thereof. The tablet 10 has an elongated tablet body 11 having a length greater than its width. The tablet body includes an elongated central body part 12 of a finite and uniform thickness and having an outwardly facing, smooth and uninterrupted perimetrical surface 13 extending parallel to a theoretical line 14 (FIG. 3) extending through a geometric center of the tablet and parallel to the section line VIII—VIII in FIG. 5. Further characteristics of the theoretical line will be explained in more detail below. The central body part 12 is generally of an oblong, almost rectangular shape with rounded corners as shown in FIGS. 3 and 4. Further, the central body part 12 has a flat top surface 16 and a flat bottom surface 17.

The top surface 16 of the central body part 12 has a layer 18 of material of uniform thickness provided thereon along the length thereof. The upper peripheral edges of the layer 18 are rounded as at 19. Three laterally extending scores or breaking grooves 21 are provided in the layer 18 at equidistantly spaced intervals along the length of the tablet to divide the layer 18 into four equal sections. The upper surface of the layer 18 is flat and parallel to the surface 16. The scores or breaking grooves 21 have a depth that is approximately one fourth to one half the thickness of the layer 18, preferably one third the thickness. Further, the breaking grooves have an arcuate contour conforming to the rounded peripheral edge at both ends of the breaking grooves. The included angle $\theta$ between the sidewalls of the breaking grooves 21 is in the range of 70° to 110°, preferably 90°.

The bottom surface of the central body part 12 has a layer 22 of material provided thereon along the length thereof. Into the bottom facing surface of the layer 22 there is provided a pair of arcuately contoured concavities 23 and 24. The provision of the arcuately contoured concavities 23 and 24 in the bottom facing surface of the layer 22 leaves three raised surface portions 26, 27 and 28 at the opposite longitudinal ends of each concavity. The downwardly facing surface of each arcuately contoured concavity 23 and 24 is smooth between the raised surfaces 26, 27, and 27, 28 except for the provision of a breaking groove 29 in the concavity 23 and a breaking groove 31 in the concavity 24. Each breaking groove 29 and 31 extends laterally of the tablet in a direction perpendicular to the longitudinal axis of the drug tablet 10. Further, the breaking grooves 29 and 31 are both located at the apex of the arcuately contoured concavities 23 and 24 and the depth of each groove extends to but not beyond the bottom surface 17 of the central body part 12 as illustrated in FIG. 5.

The raised surface portion 27 in the central region of the bottom facing surface also has a breaking groove 32 therein that extends laterally of the tablet parallel to the breaking grooves 29 and 31. The breaking groove 32 divides the raised surface portion 27 into two raised parts 33 and 34 of equal proportion. The breaking groove 32 has a depth such that the apex of the V-like bottom is spaced approximately 0.005 inches from the bottom surface 17 of the central body part 12 as illustrated in FIG. 5. The included angle $\phi$ (FIG. 9) between the sidewalls of the breaking grooves 29 and 31 is in the range of 70° to 110°, preferably 90°. The included angle $\alpha$ (FIG. 5) between the sidewalls of the breaking groove 32 is in the range of 60° to 100°, preferably 80°.

Each of the three breaking grooves 29, 31 and 32 are aligned with a respective one of the three breaking grooves 21 so that vertical cutting planes perpendicular to the longitudinal axis of the tablet and extending through each aligned pair of breaking grooves 21, 29; 21, 32; and 21, 31 will divide the tablet into four equal sections 36, 37, 38 and 39.

When the tablet 10 is placed so that the raised surface portions 26 and 28 rest on a flat surface 41 (FIG. 5), a gap or spacing X exists between the raised parts 33 and 34 and the flat surface 41. This space or gap is insufficient, however, for facilitating a fracturing of the tablet along the aligned breaking grooves 21, 32 when a force is applied to the upper surface of the layer 18 at the central breaking groove 21.

The spacing between the bottom of each of the breaking grooves 21 and the bottom of the aligned one of the breaking grooves 29, 31 and 32 define a zone of weakness generally referred to by the reference numerals 42, 43 and 44. A cross section of the zones of weakness 42 and 43 are shown in FIGS. 7 and 8. Thus, when the tablet is grasped by a user between the thumb and forefinger of each hand, an appropriate force can be applied to effect a fracturing of the tablet along the zone of weakness 43, namely, along a plane defined by the aligned breaking grooves 21 and 32. This is schematically represented in FIG. 9. Following a separating of the tablet 10 into two half sections 46 and 47, one of the half sections, such as the half section 46 in FIG. 10, can be positioned so that the raised surfaces 26 and 33 rest on a supporting surface 41. In other words, the concavity 23 faces the supporting surface 41. A pencil or finger of the user can then be used to apply a force in direction of the arrow P to the aligned breaking grooves 21 and 29 to effect a fracturing of the half section into two quarter sections 48 and 49.

In the alternative, the half sections 46 and 47 can be simultaneously fractured into quarter sections utilizing a different methodology. For example, and referring to FIG. 11, the half sections 46 and 47 are positioned so that the raised surfaces 26 and 33 engage respectively the raised surfaces 28 and 34. In other words, the concavities 23 and 24 face one another. In addition, the aligned set of breaking grooves 21 and 29 on the half section 46 are parallel to and congruent with the aligned set of breaking grooves 21 and 31 on the half section 46. A placement of this stacked arrangement between the thumb and forefinger of a user's hand will, upon the application of a compressive or pinching force in the direction of the arrows F and T will effect a simultaneous fracturing of the half sections 46 and 47 into four quarter sections 48, 49, 51 and 52.

During each of the aforementioned fractures, a fracturing of the tablet 10 into half sections 46 and 47 results in the tablet having the requisite active pharmacological agents in each half and within the requisite limits of ±15%. Similarly, a fracturing of the half sections 46 and 47 into quarter sections also results in each quarter section having the requisite active pharmacological agent within the prescribed ±15% limit.

Figure 14:
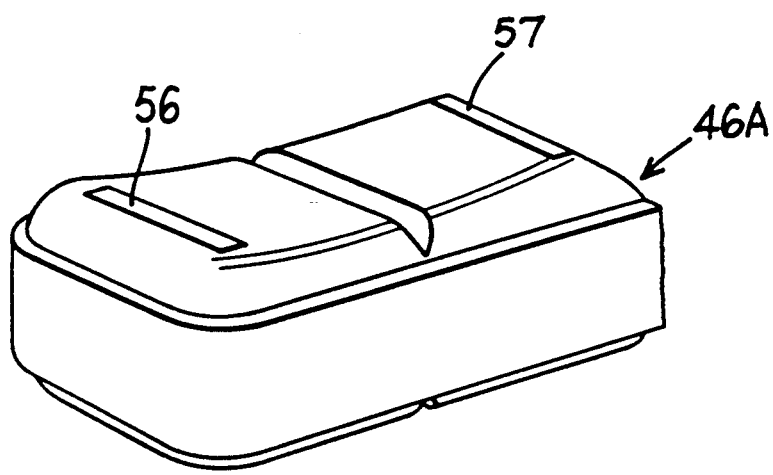
FIG. 14 illustrates a half section having a flat end surface, so that the opposing ends of the half section will engage along or at opposing flat surfaces.
Figure 15:
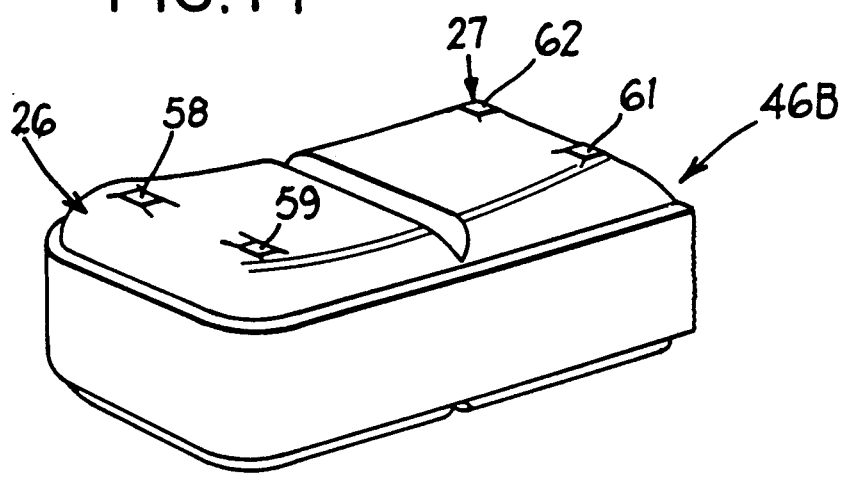
FIG. 15 illustrates a half section having a pair of laterally spaced pads with flat surfaces, so that the opposing ends of the half sections will engage at the opposing pads.

FIGS. 13 to 15 illustrate a half section, such as the half section 46. In order to differentiate between each of the half sections illustrated in these figures, the reference numeral 46 has been utilized to identify the half section in FIG. 13 whereas the suffix "A" and "B" have been added to the reference numeral 46 in FIGS. 14 and 15. In the embodiment illustrated in FIG. 13, a pair of lines 53 and 54 are illustrated and represent the lines whereat engagement of the half section 46 occurs with either a flat surface 41 or the other half section 47 when in a stacked arrangement, such as is illustrated in FIG. 11. Both half sections would, therefore, engage at lines congruent with the lines 53 and 54 illustrated in FIG. 14.

In the embodiment of FIG. 14, the half section 46A has a pair of flat surface areas 56 and 57 thereon. Thus, the half section 46A can be oriented so that the flat surfaces 56 and 57 rest on the flat surface 41 or corresponding flat surfaces of the other half section when the half sections are positioned in a stacked arrangement, such as illustrated in FIG. 11.

In the embodiment illustrated in FIG. 15, four surface pads 58, 59, 60 and 61 are provided at the raised surface portions 26 and 27. The surface pads 58 are flat surfaces that are raised above the upper most height of the raised surface portions 26 and 27. Thus, the surface pads 58, 59, 60 and 61 will rest on a flat surface when the half section is placed in the position illustrated in FIG. 10. Similarly, the aforementioned surface pads will rest on corresponding surface pads of the other half section when the half sections are stacked in the arrangement such as illustrated in FIG. 11.

Although particular preferred embodiments of the invention have been disclosed in detail for illustrative purposes, it will be recognized that variations or modifications of the disclosed tablet lie within the scope of the present invention.

The embodiments of the invention in which an exclusive property or privilege is claimed are defined as follows:

1. A tri-scored drug tablet, comprising:
   an elongated tablet body having a length greater than its width, said body having top and bottom surfaces;
   a pair of concavities in said bottom surface, said top surface being flat, each concavity being equal in size and having parallel major and minor axes, each concavity further having a smooth and uninterrupted arcuate surface extending between the opposite longitudinal ends of said body and a longitudinally central part of said tablet, said opposite longitudinal ends of said body and said longitudinally central part being of a thicker dimension than the thickness of said body measured at an apex of each of said concavities; and
   aligned breaking grooves formed in said top and bottom surfaces at both of said concavities and between said concavities at said longitudinally central part, each said breaking groove extending laterally across the width of said tablet at said apex of each of said concavities and at said longitudinally central part, so that upon a user grasping both ends of said tablet between a forefinger and a thumb on each hand, a force is applied to effect a fracture of said tablet along said groove at said longitudinally central part to divide said tablet into two half sections, said user thereafter placing said two half sections in a stacked arrangement so that said two concavities face one another and said thicker dimensioned portions at the longitudinal ends of said half sections are in engagement, said user thereafter applying a compressive force to the midpoint of said stacked half sections to effect a simultaneous fracture of each of said halves along said breaking grooves at said apexes of said concavities to divide each of said half sections into two quarter sections, each section containing within ±15% by weight of a prescribed limit of pharmacological agent.

2. The tri-scored drug tablet according to claim 1, wherein said tablet body includes an elongated central body part of a finite and uniform thickness and having an outwardly facing, smooth and uninterrupted perimetrical surface extending parallel to a theoretical line perpendicular to said top surface and extending through a geometric center of said tablet, wherein each said thicker dimensioned portions at each end of said bottom surface of each half section of said central body part including a region defined by a surface part, between which surface parts is provided said concavity, the depth of each of said concavities being less than the highest height dimension of said surface parts;
   wherein said breaking grooves in said concavities and at said longitudinally central part of said bottom surface have a depth that extends from said apex of each of said concavities to a bottom surface of said central body part; and
   wherein each of said breaking grooves in said top surface has a depth that extends approximately one fourth to one half the distance between said top surface and a top surface of said central body part.

3. The tri-scored drug tablet according to claim 2, wherein said breaking grooves in said top surface extend one third the distance between said top surface and said top surface of said central body part.

4. The tri-scored drug tablet according to claim 1, wherein said major axis of each of said concavities extends parallel to a longitudinal axis of said elongated tablet body.

* * * * *

UNITED STATES PATENT AND TRADEMARK OFFICE
CERTIFICATE OF CORRECTION

PATENT NO. : 5,061,494
DATED : October 29, 1991
INVENTOR(S) : Phillip F. NI et al.

It is certified that error appears in the above-identified patent and that said Letters Patent is hereby corrected as shown below:

Title page, item [73] change the assignee name from "The Upjohn Comany" to ---The Upjohn Company---.

On the title page, insert the following information:

[63] Continuation of pct/US88/04367, filed Dec. 12, 1988.

Signed and Sealed this

Twenty-second Day of March, 1994

Attest:

BRUCE LEHMAN

Attesting Officer   Commissioner of Patents and Trademarks